(12) United States Patent
Jaiswal et al.

(10) Patent No.: US 11,523,761 B2
(45) Date of Patent: Dec. 13, 2022

(54) METHOD AND SYSTEM FOR ASSESSMENT OF COGNITIVE WORKLOAD USING BREATHING PATTERN OF A PERSON

(71) Applicant: Tata Consultancy Services Limited, Mumbai (IN)

(72) Inventors: Dibyanshu Jaiswal, Kolkata (IN); Debatri Chatterjee, Kolkata (IN); Arijit Chowdhury, Kolkata (IN); Rahul Gavas, Bangalore (IN); Tanushree Banerjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 245 days.

(21) Appl. No.: 16/889,871

(22) Filed: Jun. 2, 2020

(65) Prior Publication Data

US 2020/0383624 A1    Dec. 10, 2020

(30) Foreign Application Priority Data

Jun. 6, 2019   (IN) .............................. 201921022528

(51) Int. Cl.
*A61B 5/16* (2006.01)
*A61B 5/024* (2006.01)
(Continued)

(52) U.S. Cl.
CPC .......... *A61B 5/165* (2013.01); *A61B 5/02416* (2013.01); *A61B 5/0816* (2013.01);
(Continued)

(58) Field of Classification Search
CPC ... A61B 5/165; A61B 5/02416; A61B 5/0816; A61B 5/7267; A61B 5/7278; A61B 5/742; A61B 5/4884
See application file for complete search history.

(56) References Cited

U.S. PATENT DOCUMENTS

2017/0086729 A1 * 3/2017 Bruno ................ A61B 5/16
2019/0259290 A1 * 8/2019 Lynch .................. G06N 7/005

FOREIGN PATENT DOCUMENTS

CN          107122643 A      9/2017
WO    WO 2017210873 A1    12/2017

OTHER PUBLICATIONS

Zhao, X. et al. (2013). "Feature Selection with Attributes Clustering by Maximal Information Coefficient," *Procedia Computer Science*, vol. 17; pp. 70-79.

(Continued)

*Primary Examiner* — Hongmin Fan
(74) *Attorney, Agent, or Firm* — Finnegan, Henderson, Farabow, Garrett & Dunner, LLP (57) ABSTRACT

This disclosure relates generally to assessment of cognitive workload using breathing pattern of a person, where cognitive workload is the amount of mental effort required while doing a task. The method and system provides assessment of cognitive workload based on breathing pattern extracted from photoplethysmograph (PPG) signal, which is collected from the person using a wearable device. The PPG signal collected using the wearable device are processed in multiple stages that include breathing signal extraction to extract breathing pattern. The extracted breathing pattern is used for assessment of cognitive workload using a generated personalized training model, wherein the personalized training model is generated and dynamically updated for each person based on selection of a sub-set of breathing pattern features using feature selection and classification techniques that include maximal information coefficient (MIC) techniques. Finally based on personalized training model, the extracted breathing pattern is classified as high cognitive workload or low cognitive workload.

13 Claims, 10 Drawing Sheets

(51) Int. Cl.
*A61B 5/08* (2006.01)
*A61B 5/00* (2006.01)
(52) U.S. Cl.
CPC .......... *A61B 5/7267* (2013.01); *A61B 5/7278* (2013.01); *A61B 5/742* (2013.01)

(56) References Cited

OTHER PUBLICATIONS

3152MUM2013-CS Spec, Publication Date Jul. 3, 2015, by Tata Consulting Services.

* cited by examiner

METHOD AND SYSTEM FOR ASSESSMENT OF COGNITIVE WORKLOAD USING BREATHING PATTERN OF A PERSON

CROSS-REFERENCE TO RELATED APPLICATIONS AND PRIORITY

The present application claims priority from Indian provisional application no. 201921022528, filed on Jun. 6, 2019.

TECHNICAL FIELD

The disclosure herein generally relates to field of assessment of cognitive workload of a person and, more particularly, to assessment of cognitive workload of a person using the person's breathing pattern.

BACKGROUND

Cognitive or mental workload is the amount of mental effort required while doing a task. The cognitive workload directly affects the performance of an individual. A cognitive workload which is too high results in psychological conditions like stress, fatigue and anxiety, while low cognitive workload results in underutilization of one's mental resources. Hence based on cognitive workload the individual's performance declines if cognitive workload is too high or too low, resulting in mental fatigue or boredom. Therefore monitoring and assessing of an individual's cognitive workload is of immense importance to ensure effective and efficient performance standards.

The existing techniques for assessment of an individual's cognitive workload include questionnaire based assessments, numerous physiological correlates like brain activation, skin conductance and cardiovascular changes. The questionnaire based assessments may not be very effective as they are mostly structured instruments that allow little flexibility to the individual with respect to response format. Further the existing physiological correlates techniques can cause discomforts for the individual as sensors used are not unobtrusive and may not be easy to use. Further the physiological correlates techniques may not give very accurate results on complicated sensor data received. Further standardization of cognitive workload features may also not be very effective as each individual may have a different tolerance/threshold/features cognitive workload level.

SUMMARY

Embodiments of the present disclosure present technological improvements as solutions to one or more of the above-mentioned technical problems recognized by the inventors in conventional systems. For example, in one embodiment, a method and system for assessment of cognitive workload using breathing pattern of a person is provided. The method and system provides assessment of cognitive workload based on breathing pattern extracted from photoplethysmograph (PPG) signal, which is collected from the person using a wearable device. The PPG signal collected using the wearable device are processed in multiple stages that include breathing signal extraction to extract breathing pattern. The extracted breathing pattern is used for assessment of cognitive workload using a generated personalized training model, wherein the personalized training model is generated and dynamically updated for each person based on selection of a sub-set of breathing pattern features using feature selection and classification techniques that include maximal information coefficient (MIC) techniques. Finally based on personalized training model, the extracted breathing pattern is classified as high cognitive workload or low cognitive workload.

In another aspect, a method for assessment of cognitive workload using breathing pattern of a person is provided. The method includes sensing a plurality of physiological data from the person using a plurality of physiological sensors while the person is performing a pre-assigned activity. Further the method includes extracting a plurality of breathing signals from the received plurality of physiological data and extracting a plurality of breathing pattern features from the extracted plurality of breathing signals. Further the method includes selecting a subset of breathing pattern features from the extracted plurality of breathing pattern features. Further the method includes generating a personalized training model for the person based on the selected subset of breathing pattern features. Further the method includes sensing actual plurality of physiological data using the plurality of physiological sensors while the person is performing the pre-assigned activity. Further the method includes extracting plurality of actual breathing signals from the received actual plurality of physiological data. Further the method includes extracting plurality of actual breathing pattern features from the extracted actual plurality of breathing signals. Further the method includes classifying the actual breathing pattern features of the person into high cognitive workload or low cognitive workload using the personalized training model and displaying the classified actual breathing pattern features.

In another aspect, a system for assessment of cognitive workload using breathing pattern of a person is provided. The system comprises a memory storing instructions and a centralized database, one or more communication interfaces; and one or more hardware processors coupled to the memory via the one or more communication interfaces, wherein the one or more hardware processors are configured by instructions to include a pre-processing module a a plurality of physiological sensors for sensing a plurality of physiological data and an actual plurality of physiological data from the person using while the person is performing a pre-assigned activity. The system further comprises a task database comprises of an exhaustive list of tasks and their respective cognitive load. The system further comprises a breathing signal extractor in a extractor for extracting a plurality of breathing signals from the received plurality of physiological data and for extracting plurality of actual breathing signals from the received actual plurality of physiological data. The system further comprises a breathing pattern extractor in the extractor for extracting a plurality of breathing pattern features from the extracted plurality of breathing signals and for extracting plurality of actual breathing pattern features from the extracted actual plurality of breathing signals. The system further comprises a feature selector for selecting a subset of breathing pattern features from the extracted plurality of breathing pattern features. The system further comprises a personalized training model generator for generating a personalized training model for the person based on the selected subset of breathing pattern features. The system further comprises a dynamic classifier for classifying the actual breathing pattern features of the person into high cognitive workload or low cognitive workload using the personalized training model and a display module displaying the classified actual breathing pattern features as high cognitive workload or low cognitive workload.

Another embodiment provides a non-transitory computer-readable medium having embodied thereon a computer program for a computer readable program, wherein the computer readable program, when executed by one or more hardware processors, causes estimation of remaining useful life in lithium based batteries. The program includes sensing, by one or more hardware processors, a plurality of physiological data from the person using a plurality of physiological sensors while the person is performing a pre-assigned activity. Further the method includes extracting a plurality of breathing signals from the received plurality of physiological data and extracting a plurality of breathing pattern features from the extracted plurality of breathing signals. Further the method includes selecting a subset of breathing pattern features from the extracted plurality of breathing pattern features. Further the method includes generating a personalized training model for the person based on the selected subset of breathing pattern features. Further the method includes sensing actual plurality of physiological data using the plurality of physiological sensors while the person is performing the pre-assigned activity. Further the method includes extracting plurality of actual breathing signals from the received actual plurality of physiological data. Further the method includes extracting plurality of actual breathing pattern features from the extracted actual plurality of breathing signals. Further the method includes classifying the actual breathing pattern features of the person into high cognitive workload or low cognitive workload using the personalized training model and displaying the classified actual breathing pattern features.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 7A and FIG. 7B, where similar reference characters denote corresponding features consistently throughout the figures, there are shown preferred embodiments and these embodiments are described in the context of the following exemplary system and/or method.

Figure 1:
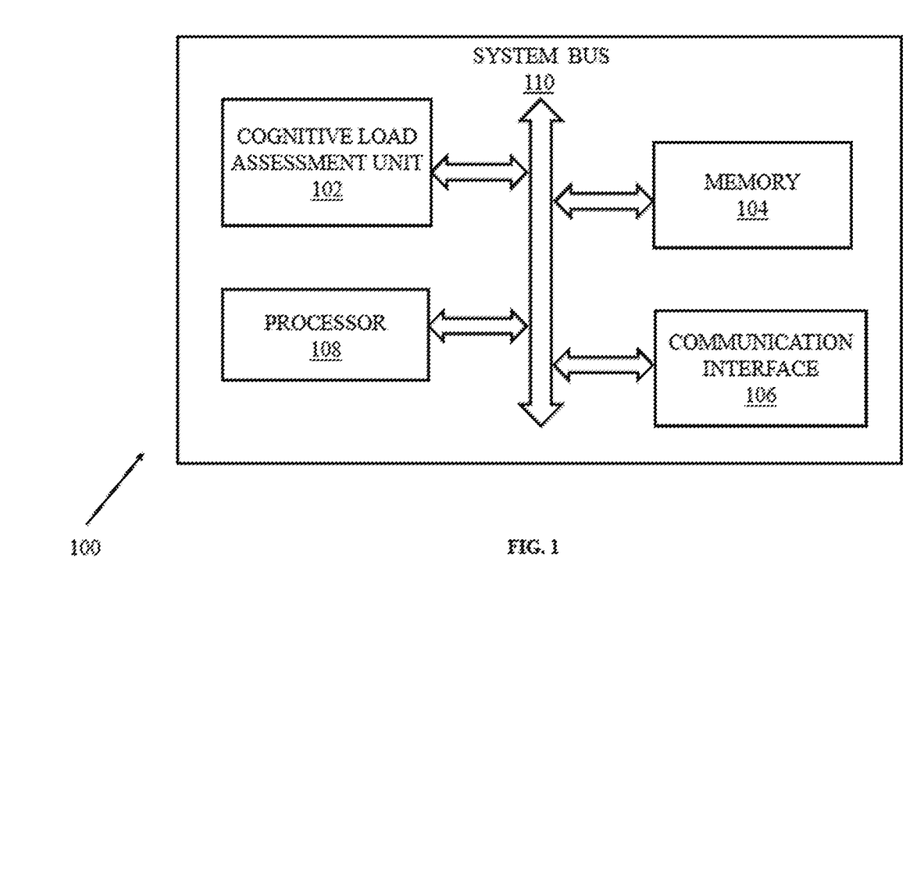
FIG. 1 illustrates an exemplary block diagram of a system for assessment of cognitive workload using breathing pattern of a person in accordance with some embodiments of the present disclosure.

FIG. 1 is a block diagram of a system 100 for assessment of cognitive workload using breathing pattern of a person, in accordance with an example embodiment. The system 100 includes a cognitive workload assessment unit 102 for mining rule intents from documents. The cognitive workload assessment unit 102 includes or is otherwise in communication with a memory 104, a communication interface 106, and a processor 108. The memory 104, communication interface 106, and the processor 108 may be coupled by a system bus 110 or a similar mechanism. Although FIG. 1 shows example components of cognitive workload assessment unit 102, in other implementations, system 100 may contain fewer components, additional components, different components, or differently arranged components than depicted in FIG. 1.

The processor 108 may be implemented as one or more microprocessors, microcomputers, microcontrollers, digital signal processors, central processing units, state machines, logic circuitries, and/or any devices that facilitates in designing polymeric carrier for controlled release of molecules. Further, the processor 108 may comprise a multi-core architecture. Among other capabilities, the processor 108 is configured to fetch and execute computer-readable instructions or modules stored in the memory 104. The processor 108 may include circuitry implementing, among others, audio and logic functions associated with the communication. For example, the processor 108 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 108 thus may also include the functionality to encode messages and/or data or information. The processor 108 may include, among other things, a clock, an arithmetic logic unit (ALU) and logic gates configured to support operation of the processor 108. Further, the processor 108 may include functionality to execute one or more software programs, which may be stored in the memory 104 or otherwise accessible to the processor 108.

The memory 104, may store any number of pieces of information, and data, used by the system 100 to implement the functions of the system 100. The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Examples of volatile memory may include, but are not limited to volatile random access memory (RAM). The non-volatile memory may additionally or alternatively comprise an electrically erasable programmable read only memory (EEPROM), flash memory, hard drive, or the like. The memory 104 may be configured to store information, data, applications, instructions or the like for enabling the system 100 to carry out various functions in accordance with various example embodiments. Additionally or alternatively, the memory 104 may be configured to store instructions which when executed by the processor 108 causes the system 100 to behave in a manner as described in various embodiments.

The communication interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the communication interface (s) 106 may include one or more ports. One or more functionalities of the system 100 and components thereof, is further explained in detail with respect to block diagram described in FIG. 2.

Figure 2:
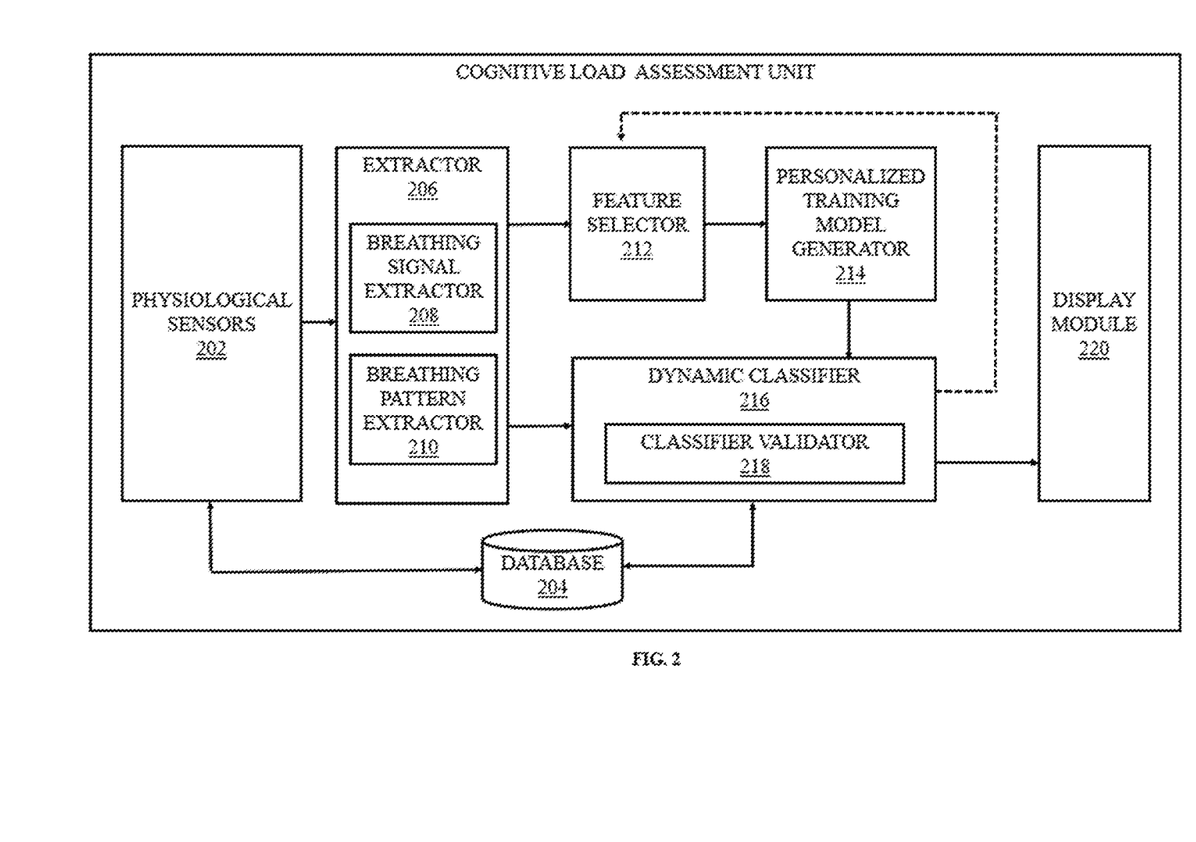
FIG. 2 is a functional block diagram of various modules stored in module(s) of a memory of the system of FIG. 1 in accordance with some embodiments of the present disclosure.

FIG. 2, with reference to FIG. 1, is a block diagram of various modules of cognitive workload assessment unit 102 of the system 100 of FIG. 1 in accordance with an embodiment of the present disclosure. In an embodiment of the present disclosure, the system 100 comprises a plurality of physiological sensors (202) for sensing a plurality of physiological data and an actual plurality of physiological data from the person using while the person is performing a pre-assigned activity. The system further comprises a database (204) or a task database (204). The database (204) comprises of an exhaustive list of tasks and their respective cognitive load. The system 100 further comprises a breathing signal extractor (208) in a extractor (206) for extracting a plurality of breathing signals from the received plurality of physiological data and for extracting plurality of actual breathing signals from the received actual plurality of physiological data. The system 100 further comprises a breathing pattern extractor (210) in the extractor (206) for extracting a plurality of breathing pattern features from the extracted plurality of breathing signals and for extracting plurality of actual breathing pattern features from the extracted actual plurality of breathing signals. The system 100 further comprises a feature selector (212) for selecting a subset of breathing pattern features from the extracted plurality of breathing pattern features. The system 100 further comprises a personalized training model generator (214) for generating a personalized training model for the person based on the selected subset of breathing pattern features. The system 100 further comprises a classifier (216) for classifying the actual breathing pattern features of the person into high cognitive workload or low cognitive workload using the personalized training model. The system 100 further comprises a display module (220) for displaying the classified actual breathing pattern features as high cognitive workload or low cognitive workload, that are implemented as at least one of a logically self-contained part of a software program, a self-contained hardware component, and/or, a self-contained hardware component with a logically self-contained part of a software program embedded into each of the hardware component that when executed perform the above method described herein.

According to an embodiment of the disclosure, the system 100 comprises the plurality of physiological sensors (202) configured for sensing a plurality of physiological data and an actual plurality of physiological data from the person using a wearable device while the person is performing a pre-assigned activity. The plurality of physiological sensors (202) that include sensors for measuring/collecting/sensing physiological parameters such as heart rate variability monitoring sensors, blood pressure monitoring sensors, oxygen monitoring sensors, heart rate monitoring sensors are present on a non-intrusive wearable device that include smart watch, head gear are attached to the person, while the person is performing an activity. In an embodiment, the plurality of physiological sensors (202) sense physiological signals from the subject that includes photoplethysmogram (PPG) signals.

Figure 3:
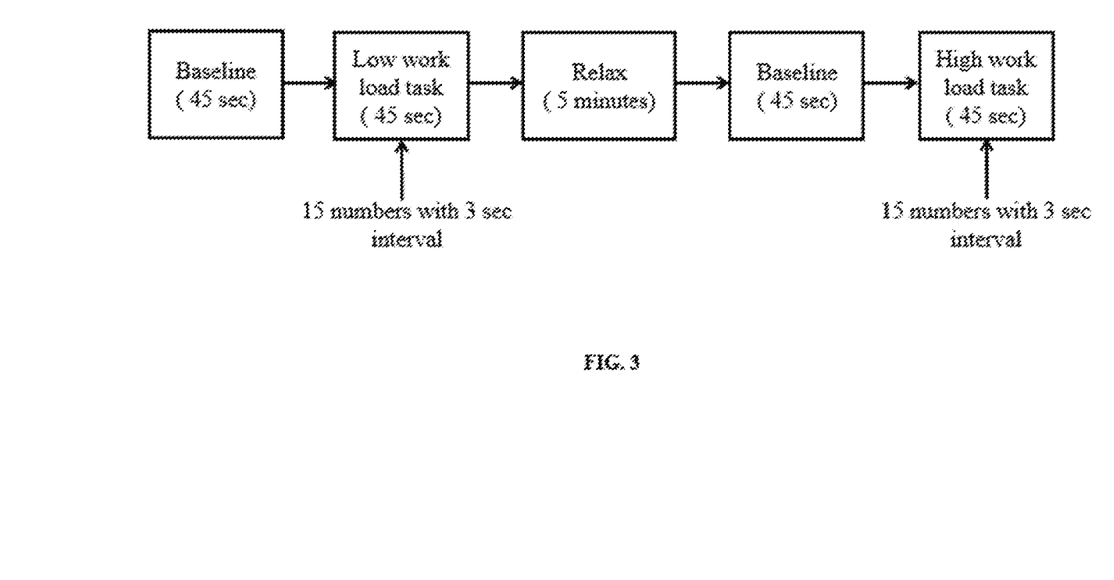
FIG. 3 illustrates, sensing a plurality of physiological data the person using a wearable device while the person is performing a pre-assigned activity according to some embodiments of the present disclosure.

The PPG signals are received from the person while the person performs the pre-assigned activity assigned by a task database (204), wherein the task database (204) comprises of an exhaustive list of tasks and their respective cognitive load and activities to be performed by the subject. The corresponding task details including task timings, duration, and difficulty level are also synced with the wearable device. In an embodiment, a non-intrusive wearable device (a smart watch such as Samsung Gear S2 Classic) is used for sensing PPG signals from a subject. The signals can be sensed in numerous ways while performing the assigned task. In an embodiment, as shown in FIG. 3, a first baseline period of 45 sec is used where at the end of this baseline period low load task is administered, while a series of 15 numbers are showed one after another with an interval of 3 seconds. During the first baseline period the subject is instructed to add them mentally and report at the end. After completion of this task, a 5 minutes relaxation time is given. Further a second baseline period of 45 seconds is followed by a high load task, hence both low and high load trials last for 45 seconds (15 numbers 3 seconds). After completing the said tasks the subject's feedback to rate the difficulty level of the tasks on a 5 point Likert Scale.

According to an embodiment of the disclosure, the system (100) further comprises the breathing signal extractor (208) in the extractor (206) configured for extracting a plurality of breathing signals from the received plurality of physiological data and for extracting plurality of actual breathing signals from the received actual plurality of physiological data. The plurality of breathing signals are extracted or reconstructed the received plurality of physiological data based on normalization techniques using filters that include $4^{th}$ order Chebyshev IIR filter.

Figure 4:
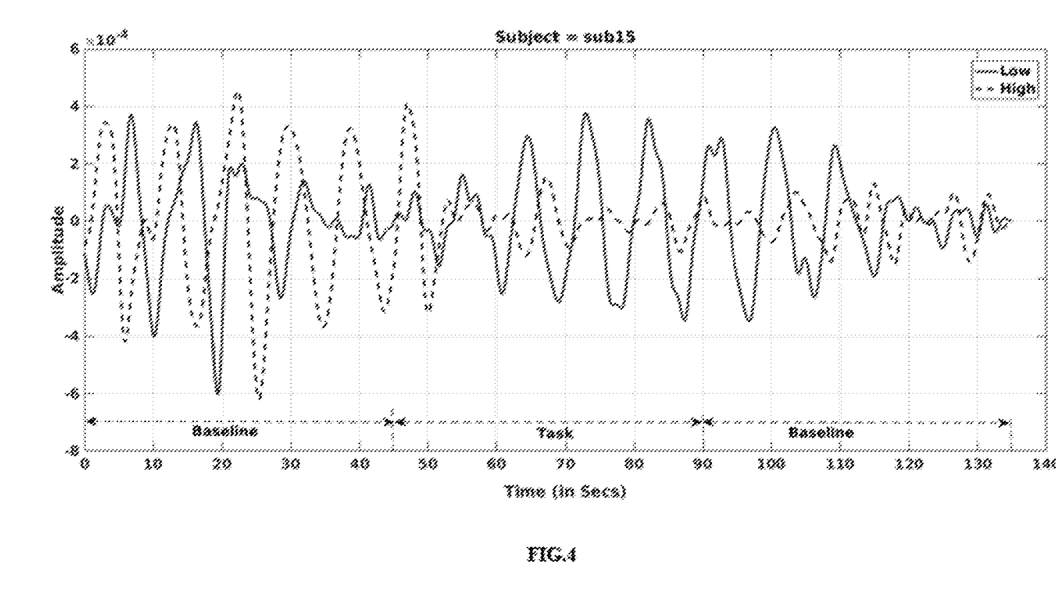
FIG. 4 illustrates, extracted breathing pattern for both low and high workload according to some embodiments of the present disclosure.

In an embodiment, physiological data is sensed at a sampling frequency of 100 Hz and the sensed PPG signal is first down sampled to 50 Hz. Further breathing pattern is reconstructed from sensed PPG signals using a 4th order Chebyshev IIR filter based on known normalization technique, with respect to maximum and minimum values of the sensed PPG signals. Further a pre-defined lower and upper cutoff frequencies of the filter are chosen to be 0.1 Hz and 0.5 Hz respectively as it corresponds to a breathing rate of 6-30 breaths/min which is well within normal breathing range of an individual. A sample extracted breathing pattern for both low and high workload for a particular person is as shown in FIG. 4.

According to an embodiment of the disclosure, the system (100) further comprises the breathing pattern extractor (210) in the extractor (206) configured for extracting a plurality of breathing pattern features from the extracted plurality of breathing signals and for extracting plurality of actual breathing pattern features from the extracted actual plurality of breathing signals. The extracted plurality of breathing pattern features include extracting standard respiratory features ($R_f$) and descriptive statistics ($S_f$) along with their subset features.

In an embodiment, a window size of 20 seconds is chosen to compute the feature vectors as this ensures at least 2 complete breathing cycles per window are captured, w.r.t to the lowest breathing rate of 6 breaths per minute. Further for every window two set of features, standard respiratory features ($R_f$) and descriptive statistics ($S_f$) along with their subset features are computed based on features extracted using frequency domain analysis techniques. The frequency domain analysis of breathing pattern signal provide breathing rate and band power of the signal. Based on the variations observed in amplitudes and intervals of peaks and troughs of the extracted breathing pattern, few more features that include peak amplitude, trough amplitude, peak intervals and trough intervals are extracted. Further features including mean, median, standard deviation etc. as well as few other features higher order statistical features such as skewness and kurtosis are also extracted, which are a representation of the dataset in skewness square versus kurtosis plane. Further Sample entropy and Spectral entropy of the PPG signal are also extracted. Further extracted standard deviation, mean, skewness and kurtosis from the normalized power distribution of the reconstructed breathing signal as normalized power distribution of a signal in frequency domain can be treated as a probability distribution. Further the fast fourier transform (FFT) peak and the ratio of 1st and 2nd FFT peaks are also extracted as features.

In an embodiment, standard respiratory features ($R_f$) are extracted by first extracting statistical features that include median, standard deviation, minimum, maximum, first quartile and third quartile from peak amplitude, trough amplitude, peak intervals and trough intervals that were extracted previously by frequency domain analysis. Hence a set of 24 (6*4) features are extracted for which an additionally, total number of peaks and troughs are also included to result in in the standard respiratory features ($R_f$) feature set. Hence, a total of 28 respiratory feature are obtained from breathing pattern signal, which can be represented as shown below;

$|R_f|=28$

In an embodiment, the features extracted as mentioned above including the features extracted using frequency domain analysis and normalization power distribution of the reconstructed breathing signal are computed on the original time series breathing pattern as well as upto $n^{th}$ derivative of the signal, wherein in an embodiments up to $4^{th}$ derivative of sensor data. Thus a total of 90 descriptive statistical features (18 features*5 signals that is the breathing signal and 4 derivatives of it). The descriptive statistics ($S_f$) can be represented as shown below:

$|S_f|=90$

A merged feature set ($M_f$), as combination of both respiratory feature and statistical features can be expressed as shown below;

$|M_f|=R_f \cup S_f$ $|M_f|=|R_f|+|S_f|=28+90=118$

According to an embodiment of the disclosure, the system 100 further comprises the feature selector (212) for selecting a subset of breathing pattern features from the extracted plurality of breathing pattern features. The selection of the subset of breathing pattern features in the feature selector (212) is based on feature selection and classification techniques that include maximal information coefficient (MIC) techniques. Further based on the feature selection a variety of classifiers are built dynamically to be used for classification. The dynamic classifiers built are known in art including Sequential Minimal Optimization (SMO), Random Forest (RF), Multilayer Perceptron (MLP), decision tress, LibSVM, Logistic Model Trees (LMT), Hoeffding Tree (HT) and for classification. An embodiment for feature selection and classification techniques are explained in the sections below.

Figure 5A:
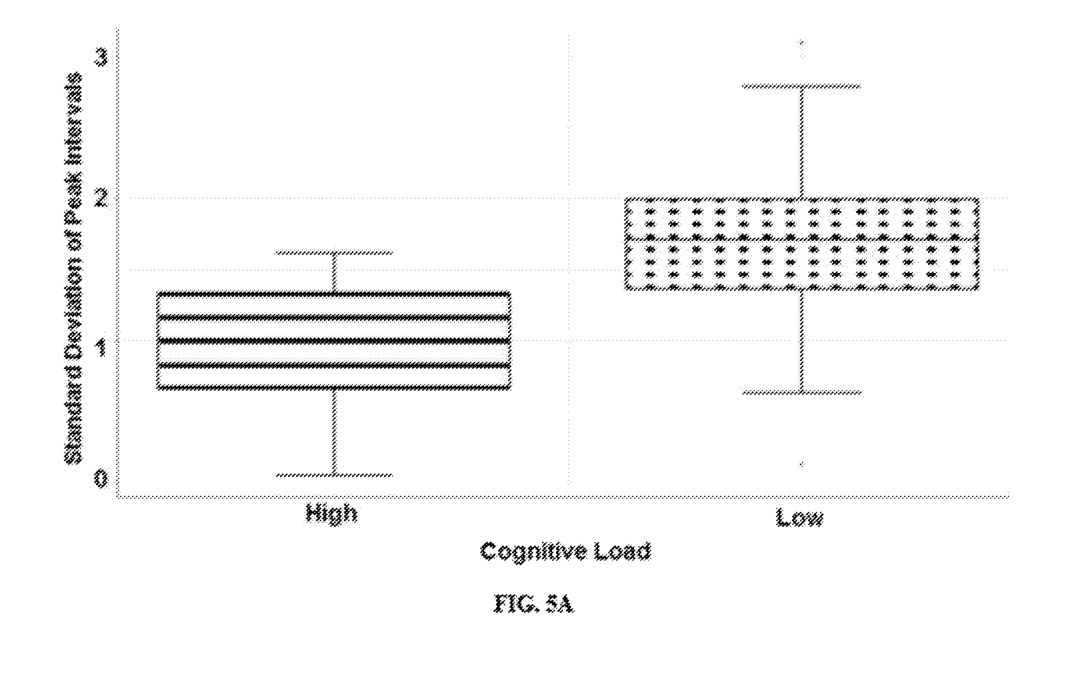
FIG. 5A, FIG. 5B and FIG. 5C illustrates, feature selection from extracted breathing pattern according to some embodiments of the present disclosure.
Figure 5B:
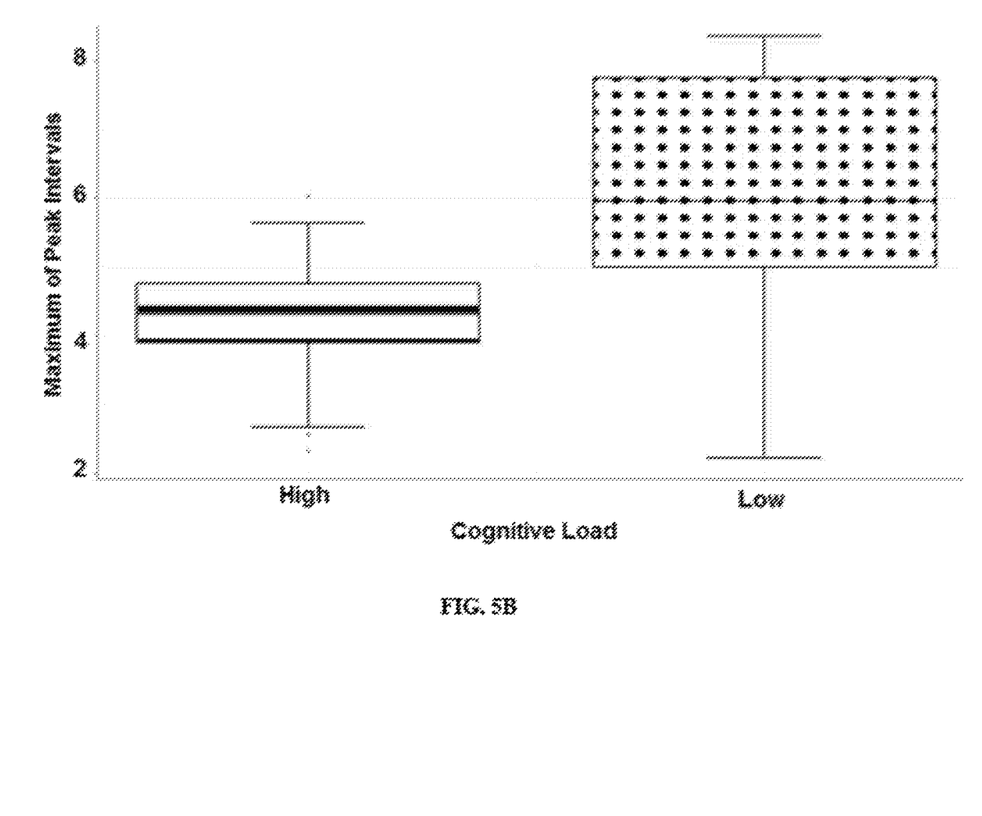
Figure 5C:
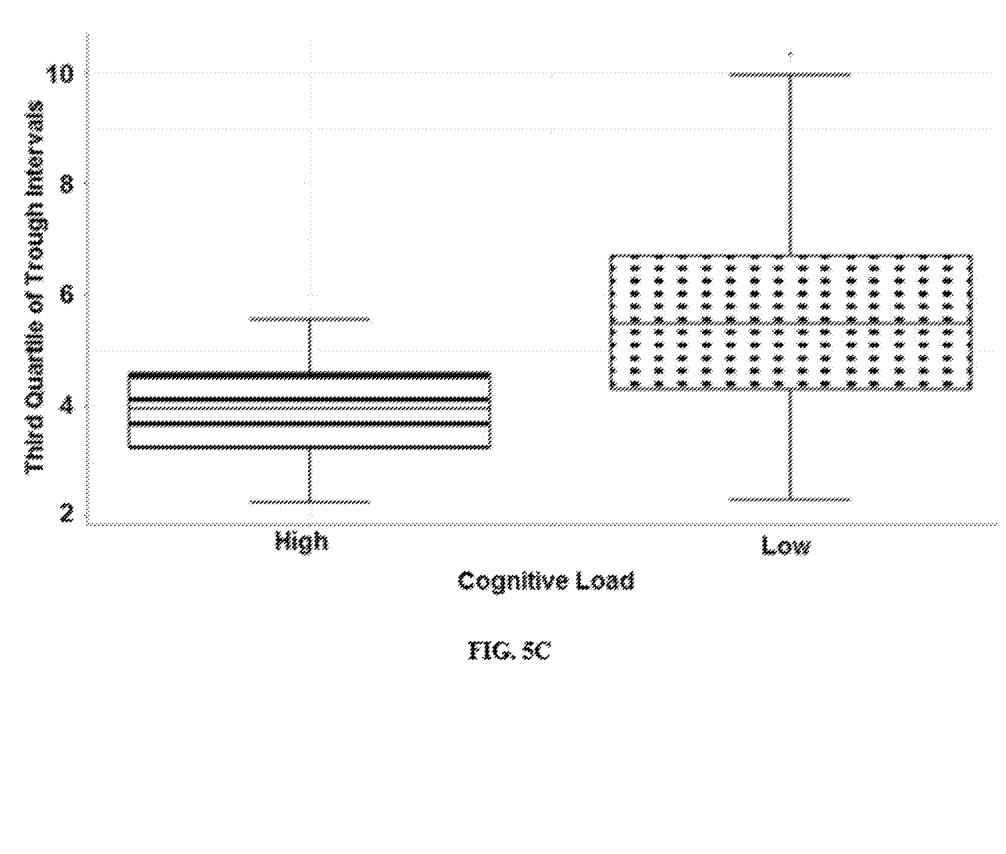

In an embodiment, the extracted plurality of breathing pattern features are fed to MINE (Maximal Information Based Nonparametric Exploration) that is based MIC (maximal information coefficient) techniques to identify high and low cognitive workload. Further for computing MIC, class labels low cognitive workload and high cognitive workload are converted into binary variables 0 and 1 respectively and each breathing pattern feature can have a MIC value in the range (0, 1) with respect to class label (low cognitive workload or high cognitive workload) as shown in FIG. 5A, FIG. 5B and FIG. 5C, wherein the Y-Axis represents a feature that includes standard deviation of peak interval, Maximum peak interval and third quartile of trough intervals, and the X-axis represents cognitive load.

In an embodiment, MIC classifies sub-features for classifying low and high load, wherein considering an use case example with respect to merged feature ($M_f$) dataset, a mean MIC value obtained is pre-determined to be 0.28 with standard deviation of 0.12. Hence, the features having MIC values greater than 0.4 (mean and standard) are selected for further analysis including $R_f$ and $S_f$ for analysis purpose and since MIC is a measure of a feature with respect the class label and is independent of other features, selected features $R_{f\_MIC}$ and $S_{f\_MIC}$ combined were equivalent to $M_{f\_MIC}$ as shown below;

$R_{f\_MIC}=\{r_i \in R_f | \text{MIC value of } r_i > 0.4\}$ $S_{f\_MIC}=\{s_i \in S_f | \text{MIC value of } S_i > 0.4\}$ $M_{f\_MIC}=\{m_i \in M_f | \text{MIC value of } m_i > 0.4\} = R_{f\_MIC} \cup S_{f\_MIC}$ Further sub-sets are selected from the features selected based on MIC by a correlation technique based on feature selection methods (FSM). A variety of FSM techniques are applied including well-known FSM such as filter method, wrapper method, Boruta. In an embodiment Boruta package of R is implemented for selecting features as it gives a variable importance measure for each feature and hence makes the process more efficient.

According to an embodiment of the disclosure, the system 100 further comprises the personalized training model generator (214) and the dynamic classifier (216). The personalized training model generator (214) is configured for generating a personalized training model for the person based on the selected subset of breathing pattern feature and the dynamic classifier (216) is configured for classifying the actual breathing pattern features of the person into high cognitive workload or low cognitive workload using the personalized training model. The dynamic classifier (216) further comprises a classifier validator (218) that is configured to validate the dynamic classifier (216) and dynamically update the dynamic classifier (216) based on comparison of classified actual subset of breathing pattern features and the exhaustive list of tasks and their respective cognitive load.

The dynamic classifier (216) is dynamically built based on the feature selection is known in art and includes Sequential Minimal Optimization (SMO), Random Forest (RF), Multilayer Perceptron (MLP), decision tress, LibSVM, Logistic Model Trees (LMT), Hoeffding Tree (HT) and for classification outcome, a low is considered as a positive outcome and a high is considered as a negative outcome during the testing working mode. The personalized training model generated by the personalized training model generator (214) is dynamically updated based on comparison of classified actual subset of breathing pattern features and the exhaustive list of tasks and their respective cognitive load in the dynamic classifier (216). The personalized training model generator (214) generates a personalized training model for each person and also dynamically updates the personalized training generated model, depending on the working mode of the system 100, as explained in the further section with the reference to FIG. 6. In an embodiment, FIG. 6, with reference to FIGS. 1-2, is an exemplary flow diagram illustrating several working modes of system 100 that include training, testing and update.

Figure 6:
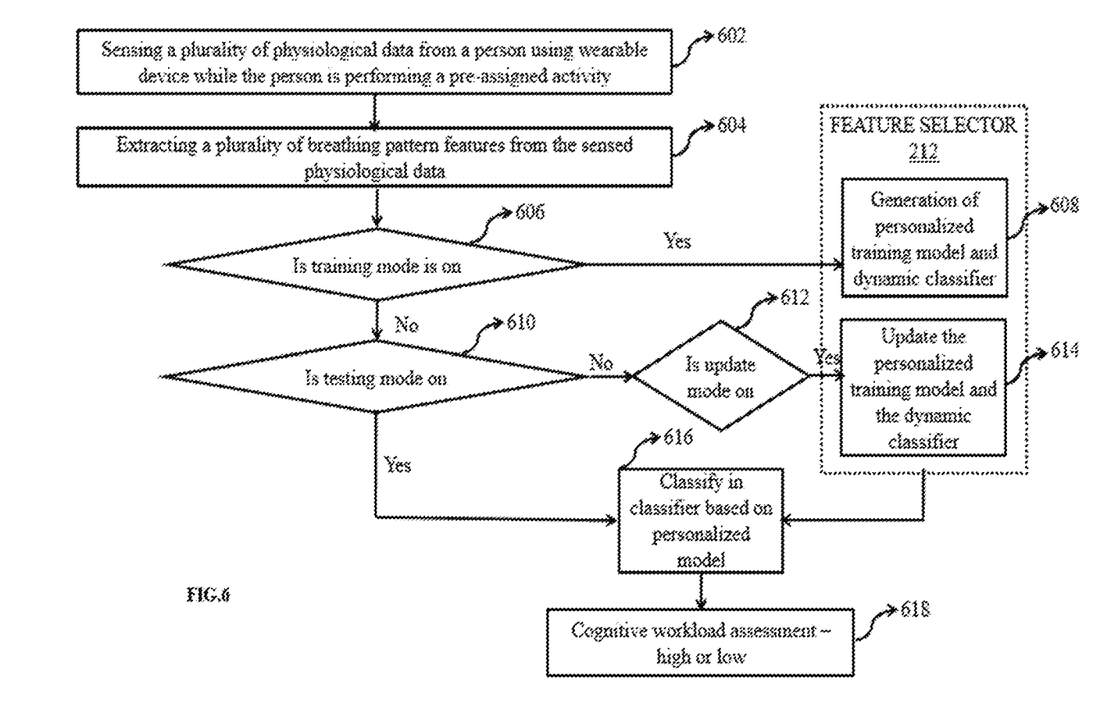
FIG. 6 illustrates, an exemplary flow diagram illustrating a method for workflow modes during assessment of cognitive workload using breathing pattern of the person using the system of FIG. 1 and FIG. 2, according to some embodiments of the present disclosure.

At step 602, a plurality of physiological data are sensed by physiological sensors (202) from a person using a plurality of physiological sensors while the person is performing a pre-assigned activity. The plurality of physiological sensors (202) are present on a non-intrusive wearable device attached to the person, while the person is performing an activity.

In the next step at 604, a plurality of breathing pattern features are extracted from the sensed physiological signals in the breathing pattern extractor (210) in the extractor (206).

In the next step at 606, the system 100 is set to training mode for a new person/user wherein for the new persona personalized training model is individually generated, while the system is not set to training mode is the user has been using the system 100.

In the next step at 608, the system 100 is set to training mode for a new person/user wherein for the new person a personalized training model and a dynamic classifier (216) is individually generated based on the selected subset of breathing pattern features as explained based on feature selection and classification techniques that include maximal information coefficient (MIC) techniques. Upon generation of personalized training model and the dynamic classifier (216), flags corresponding to personalized training model and the dynamic classifier (216) are set.

In the next step at 610, the system 100 can be set to testing mode or not set to testing mode based on the flags. Further if the system 100 is set to testing mode, it would be sent for classification into high cognitive workload or low cognitive workload, else the system 100 is not set to testing mode, it would be checked for other working modes as explained further.

In the next step at 612, the system 100 is set to update mode, wherein the personalized training model and the dynamic classifier (216) is to be dynamically updated based on classifier validator (218) that is configured to validate the dynamic classifier (216) based on comparison of classified actual subset of breathing pattern features and the exhaustive list of tasks and their respective cognitive load.

In an embodiment, if the classified actual subset of breathing pattern features from the dynamic classifier (216) for a given task is more that 70 percent of the exhaustive list of tasks and their respective cognitive load, then the dynamic classifier (216) is continued to be used as valid classifier for the given task else the dynamic classifier (216) is updated, which is represented by the dotted line as shown in FIG. 2.

In the next step at 614, if system 100 is set to update mode the personalized training model is dynamically updated individually generated based on the selected subset of breathing pattern features as explained based on feature selection and classification techniques that include maximal information coefficient (MIC) techniques.

In the next step at 616, the actual breathing pattern features of the person is classified into high cognitive workload or low cognitive workload using the dynamic classifier (216).

In the next step at 618, the classified actual breathing pattern features is displayed in the display module (220).

According to an embodiment of the disclosure, the system 100 further comprises the display module (220) that is configured for displaying the classified actual breathing pattern features as high cognitive workload or low cognitive workload.

Figure 7A:
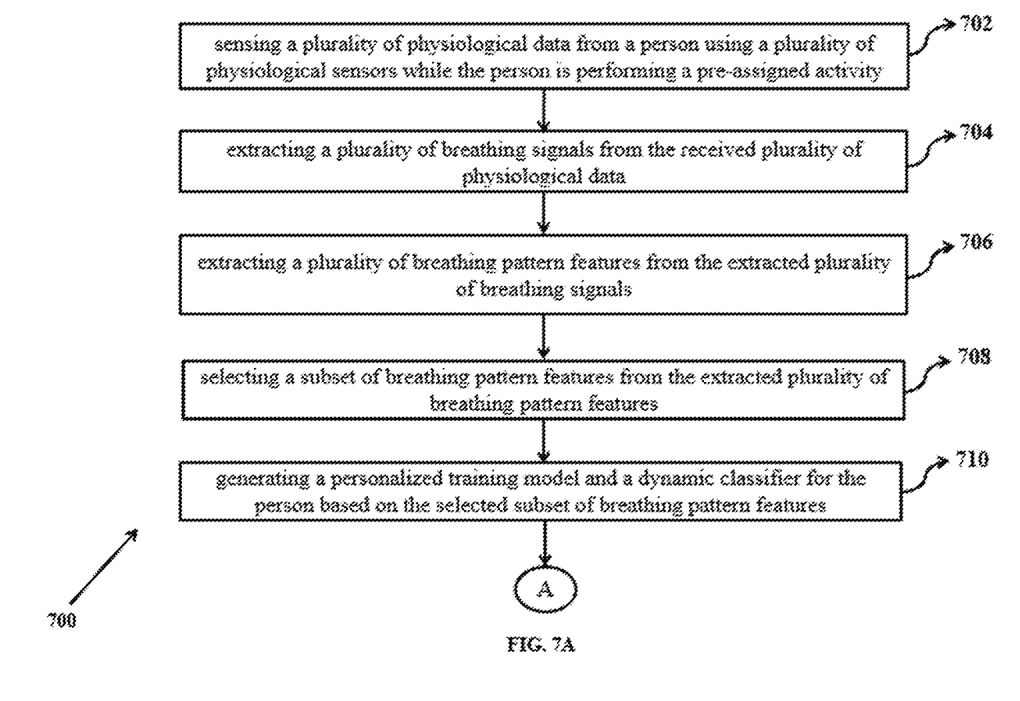
FIGS. 7A and 7B is an exemplary flow diagram illustrating a method for assessment of cognitive workload using breathing pattern of a person using the system of FIG. 1 in accordance with some embodiments of the present disclosure.
Figure 7B:
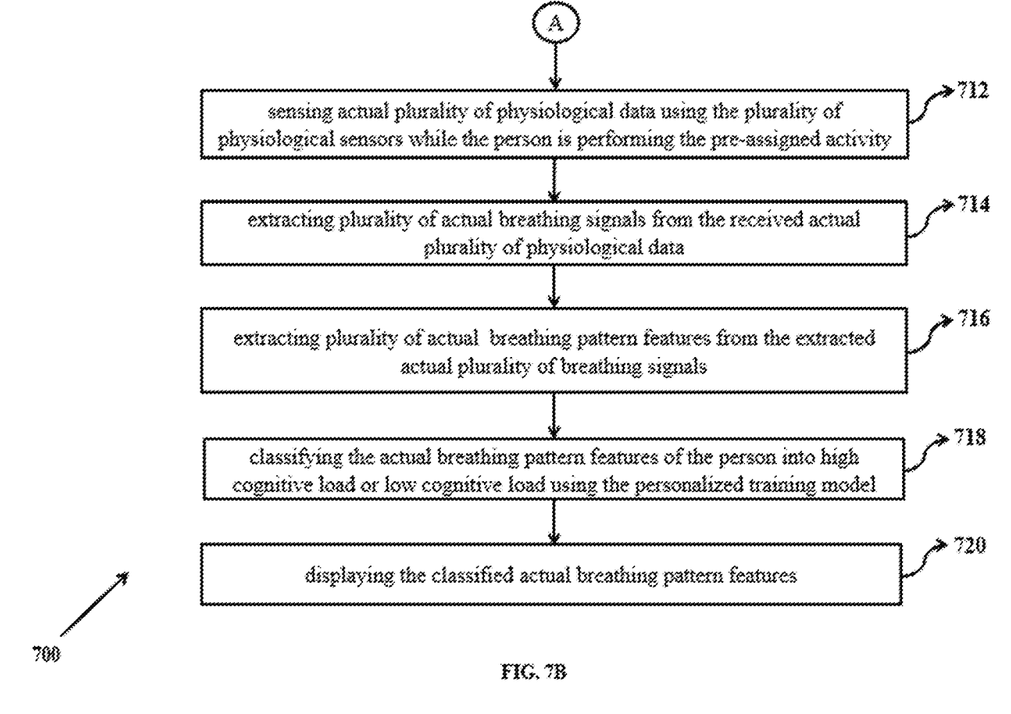

FIGS. 7A and 7B, with reference to FIGS. 1-2, is an exemplary flow diagram illustrating a method for assessment of cognitive workload using breathing pattern of a person using the system 100 of FIG. 1 according to an embodiment of the present disclosure. In an embodiment, the system 100 comprises one or more data storage devices or the memory 104 operatively coupled to the one or more hardware processors 108 and is configured to store instructions for execution of steps of the method by the one or more processors 108. The steps of the method of the present disclosure will now be explained with reference to the components of the system 100 and the modules 202-218 as depicted in FIGS. 1-2, and the flow diagram as depicted in FIGS. 7A and 7B.

At step 702, a plurality of physiological data are sensed by physiological sensors (202) from a person using a plurality of physiological sensors while the person is performing a pre-assigned activity. The plurality of physiological sensors (202) are present on a non-intrusive wearable device attached to the person, while the person is performing an activity. In an embodiment, the plurality of physiological sensors (202) sense physiological signals from the subject that includes photoplethysmogram (PPG) signals. The PPG signals are received from the person while the person performs the pre-assigned activity assigned by a task database (204), wherein the task database (204) comprises of an exhaustive list of tasks and their respective cognitive load, wherein the activities performed by the subject includes brisk walking, moving up/down stairs, cycling.

In the next step at 704, a plurality of breathing signals are extracting from the received plurality of physiological in the data breathing signal extractor (208) in the extractor (206). The plurality of breathing signals are extracted or reconstructed the received plurality of physiological data based on normalization techniques using filters that include $4^{th}$ order Chebyshev IIR filter.

In the next step at 706, a plurality of breathing pattern features are extracted from the extracted plurality of breathing signals in the breathing pattern extractor (210) in the extractor (206). The extracted plurality of breathing pattern features include extracting standard respiratory features ($R_f$) and descriptive statistics ($S_f$) along with their subset features.

In the next step at 708, a subset of breathing pattern features are selected from the extracted plurality of breathing pattern features in the feature selector (212). The selection of the subset of breathing pattern features in the feature selector (212) is based on feature selection and classification techniques that include maximal information coefficient (MIC) techniques.

In the next step at 710, a personalized training model generator (214) and dynamic classifier (216) is generated for the person based on the selected subset of breathing pattern features. The personalized training model is dynamically updated based on comparison of classified actual subset of breathing pattern features and the exhaustive list of tasks and their respective cognitive load.

In an embodiment, the system 100 works in several working modes that include training, testing and update as shown in FIG. 6. Initially for a new person/user the system first set to Training Mode, wherein for the new person a personalized training model is individually generated based on the selected subset of breathing pattern features as explained based on feature selection and classification techniques that include maximal information coefficient (MIC) techniques. Upon generation of the personalized training model, the working mode of the system is set to testing or update mode, wherein if the working mode is set to testing, then the computed features are fed to the machine learning model to classify the current mental load of the subject. Further if the working mode is set to update mode, the personalized training model is dynamically updated based on comparison of classified actual subset of breathing pattern features and the exhaustive list of tasks and their respective cognitive load.

In the next step at 712, actual plurality of physiological data is sensed using the plurality of physiological sensors (202) while the person is performing the pre-assigned activity. The plurality of physiological sensors (202) are present on a non-intrusive wearable device attached to the person, while the person is performing an activity. In an embodiment, the plurality of physiological sensors (202) sense actual physiological signals from the subject that includes photoplethysmogram (PPG) signals. The PPG signals are received from the person while the person performs the pre-assigned activity assigned by a task database (204), wherein the task database (204) comprises of an exhaustive list of tasks and their respective cognitive load, wherein the activities performed by the subject includes brisk walking, moving up/down stairs, cycling.

In the next step at 714, plurality of actual breathing signals are extracted from the received actual plurality of physiological data in the data breathing signal extractor (208) in the extractor (206). The plurality of actual breathing signals are extracted or reconstructed the received actual plurality of physiological data based on normalization techniques using filters that include $4^{th}$ order Chebyshev IIR filter.

In the next step at 716, plurality of actual breathing pattern features are extracted from the extracted actual plurality of breathing signals the breathing pattern extractor (210) in the extractor (206). The extraction of plurality of actual breathing pattern features include actual extracting standard respiratory features ($R_{fa}$) and actual descriptive statistics (S) along with their subset features.

In the next step at 718, the actual breathing pattern features of the person is classified into high cognitive load or low cognitive load using the personalized training model the dynamic classifier (216).

In the next step at 720, the classified actual breathing pattern features is displayed in the display module (220).

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Hence a method and a system for assessment of cognitive workload using breathing pattern of a person is provided. The proposed method and system provides assessment of cognitive workload based on breathing pattern extracted from photoplethysmograph (PPG) signal, which is collected from the person using a wearable device. The PPG signal collected using the wearable device are processed in multiple stages that include breathing signal extraction to extract breathing pattern. The extracted breathing pattern is used for assessment of cognitive workload using a generated personalized training model, wherein the personalized training model is generated and dynamically updated for each person based on selection of a sub-set of breathing pattern features using feature selection and classification techniques that include maximal information coefficient (MIC) techniques. Finally based on personalized training model, the extracted breathing pattern is classified as high cognitive workload or low cognitive workload.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

We claim:

1. A processor-implemented method for assessment of cognitive workload based on breathing pattern of a person, the method comprising:
    sensing a plurality of physiological data from the person using a plurality of physiological sensors while the person is performing a pre-assigned activity;
    extracting a plurality of breathing signals from the received plurality of physiological data;
    extracting a plurality of breathing pattern features from the extracted plurality of breathing signals;
    selecting a subset of breathing pattern features from the extracted plurality of breathing pattern features;
    generating a personalized training model and a dynamic classifier for the person based on the selected subset of breathing pattern features;
    sensing actual plurality of physiological data using the plurality of physiological sensors while the person is performing the pre-assigned activity;
    extracting plurality of actual breathing signals from the received actual plurality of physiological data;
    extracting plurality of actual breathing pattern features from the extracted actual plurality of breathing signals;
    classifying the actual breathing pattern features of the person into high cognitive workload or low cognitive workload using the personalized training model; and
    displaying the classified actual breathing pattern features.

2. The method of claim 1, wherein the personalized training model and dynamic classifier is dynamically updated based on comparison of classified actual subset of breathing pattern features and an exhaustive list of tasks and their respective cognitive workload.

3. The method of claim 1, wherein the plurality of physiological sensors present on a non-intrusive wearable device attached to the person.

4. The method of claim 1, wherein the person performs the pre-assigned activity assigned by a task database, wherein the task database comprises of an exhaustive list of tasks and their respective cognitive workload.

5. The method of claim 1, wherein the plurality of physiological sensor data includes photoplethysmogram (PPG) signals.

6. The method of claim 1, wherein plurality of breathing signals are extracted or reconstructed based on normalization techniques using filters that include $4^{th}$ order Chebyshev IIR filter.

7. The method of claim 1, wherein the step of extracting the plurality of breathing pattern features include extracting standard respiratory features ($R_f$) and descriptive statistics ($S_f$) along with their subset features.

8. The method of claim 1, wherein selection of the subset of breathing pattern features is based on feature selection and classification techniques that include maximal information coefficient (MIC) techniques.

9. The method of claim 1, wherein the plurality of actual breathing signals are extracted/reconstructed based on normalization techniques using filters that include $4^{th}$ order Chebyshev IIR filter.

10. The method of claim 1, wherein extracting plurality of actual breathing pattern features include actual extracting standard respiratory features ($R_{fa}$) and actual descriptive statistics ($S_{fa}$) along with their subset features.

11. A system comprising:
    a cognitive workload assessment unit for mining rule intents from documents;
    a memory for storing instructions;
    one or more communication interfaces;
    one or more hardware processors communicatively coupled to the memory using the one or more communication interfaces, wherein the one or more hardware processors are configured by the instructions to execute the one or more modules of the cognitive workload assessment unit for assessment of cognitive workload based on breathing pattern of a person, the system comprising:
        a plurality of physiological sensors for sensing a plurality of physiological data and an actual plurality of physiological data from the person using while the person is performing a pre-assigned activity;
        a breathing signal extractor in a extractor for extracting a plurality of breathing signals from the received plurality of physiological data and for extracting plurality of actual breathing signals from the received actual plurality of physiological data;
        a breathing pattern extractor in the extractor for extracting a plurality of breathing pattern features from the extracted plurality of breathing signals and for extracting plurality of actual breathing pattern features from the extracted actual plurality of breathing signals;

a feature selector for selecting a subset of breathing pattern features from the extracted plurality of breathing pattern features;

a personalized training model generator for generating a personalized training model for the person based on the selected subset of breathing pattern features;

a dynamic classifier for classifying the actual breathing pattern features of the person into high cognitive workload or low cognitive workload using the personalized training model; and a display module displaying the classified actual breathing pattern features.

12. The system of claim 11, wherein a task database pre-assigns activity to be performed by a person and the task database comprises of an exhaustive list of tasks and their respective cognitive workload.

13. A non-transitory computer-readable medium having embodied thereon a computer readable program for estimation of remaining useful life in lithium based battery wherein the computer readable program, when executed by one or more hardware processors, cause:

sensing a plurality of physiological data from the person using a plurality of physiological sensors while the person is performing a pre-assigned activity;

extracting a plurality of breathing signals from the received plurality of physiological data;

extracting a plurality of breathing pattern features from the extracted plurality of breathing signals;

selecting a subset of breathing pattern features from the extracted plurality of breathing pattern features;

generating a personalized training model and a dynamic classifier for the person based on the selected subset of breathing pattern features;

sensing actual plurality of physiological data using the plurality of physiological sensors while the person is performing the pre-assigned activity;

extracting plurality of actual breathing signals from the received actual plurality of physiological data;

extracting plurality of actual breathing pattern features from the extracted actual plurality of breathing signals;

classifying the actual breathing pattern features of the person into high cognitive workload or low cognitive workload using the personalized training model; and displaying the classified actual breathing pattern features.

* * * * *